United States Patent

Laufer et al.

Patent Number: 6,083,255
Date of Patent: Jul. 4, 2000

[54] BRONCHIAL STENTER

[75] Inventors: Michael D. Laufer, Menlo Park; Donald A. Tanaka, San Jose; Bryan E. Loomas, Saratoga; Keith M. Burger, San Francisco, all of Calif.

[73] Assignee: Broncus Technologies, Inc., Mountain View, Calif.

[21] Appl. No.: 08/994,064

[22] Filed: Dec. 19, 1997

Related U.S. Application Data

[63] Continuation-in-part of application No. 08/833,550, Apr. 7, 1997.

[51] Int. Cl.[7] ................................. A61B 17/39
[52] U.S. Cl. .................. 607/96; 607/99; 607/101
[58] Field of Search .................. 606/27–31, 41, 606/49, 50; 607/96, 98–101, 113

[56] References Cited

U.S. PATENT DOCUMENTS

| | | |
|---|---|---|
| 4,674,497 | 6/1987 | Ogasawara . |
| 4,920,978 | 5/1990 | Colvin . |
| 4,976,709 | 12/1990 | Sand ........................................... 606/5 |
| 5,103,804 | 4/1992 | Abele et al. . |
| 5,117,828 | 6/1992 | Metzger et al. . |
| 5,269,758 | 12/1993 | Taheri . |
| 5,443,470 | 8/1995 | Stern et al. . |
| 5,545,193 | 8/1996 | Fleischman et al. . |
| 5,549,559 | 8/1996 | Eshel . |
| 5,755,753 | 5/1998 | Knowlton ................................. 607/98 |
| 5,779,698 | 7/1998 | Clayman et al. . |
| 5,782,848 | 7/1998 | Lennox ................................... 606/159 |

*Primary Examiner*—Linda C. M. Dvorak
*Assistant Examiner*—Roy Gibson
*Attorney, Agent, or Firm*—Morrison & Foerster LLP

[57] ABSTRACT

A device and method for treating collapsed bronchial tubes found in patients with chronic obstructive pulmonary disease and asthma are provided. The device which has a balloon at a distal end delivers energy so that the tissue is indirectly, i.e., conductively, heated by contact with a heated surface of the balloon which has been in turn heated by a heated fluid. The method includes heating the bronchial tube to cause at least a portion of the cross links of the collagen in the wall to unlink/open and subsequently form new cross links after the collagen fibers have realigned. The procedure effectively reinforces the structural integrity of the wall and thereby prevents the lumen from collapsing.

32 Claims, 5 Drawing Sheets

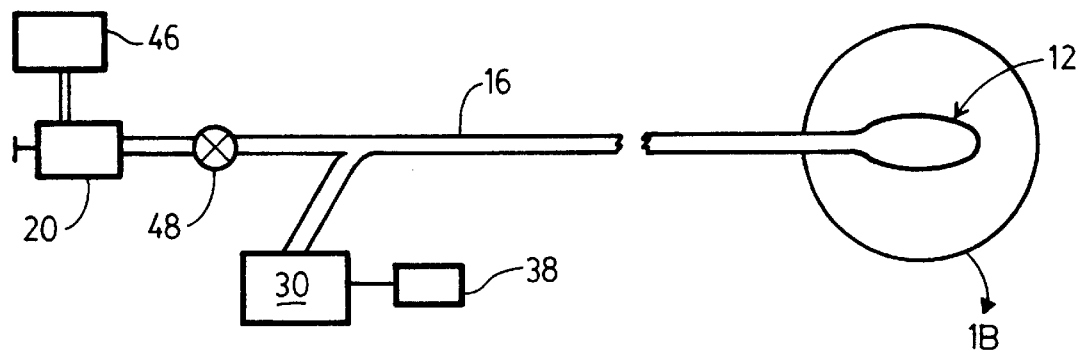
FIG._1A.
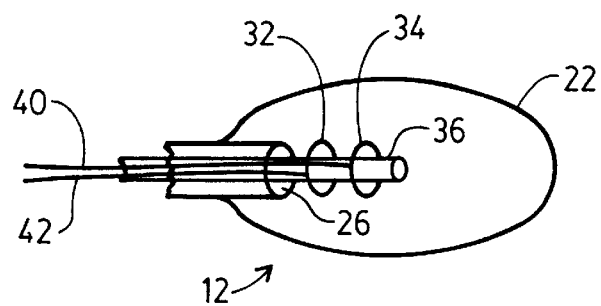
FIG._1B.
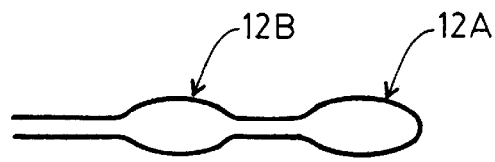
FIG._1C.

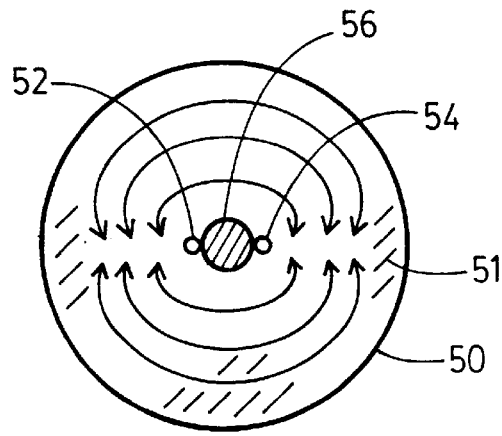
FIG._2A.
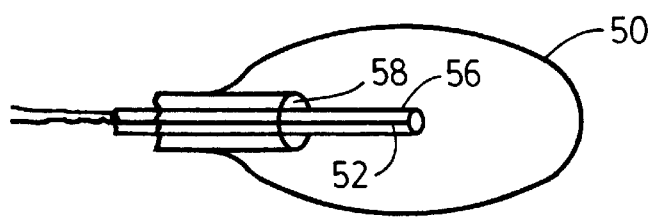
FIG._2B.
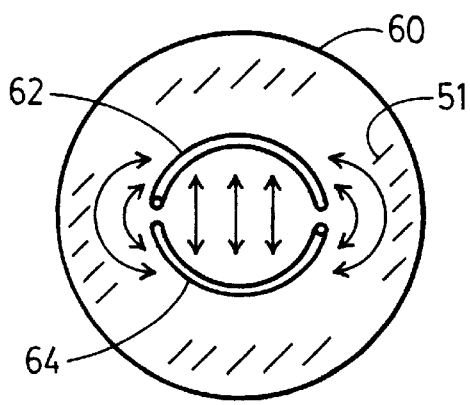
FIG._3A.
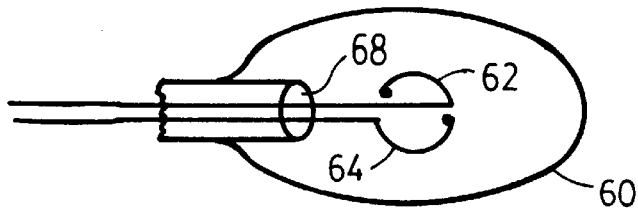
FIG._3B.

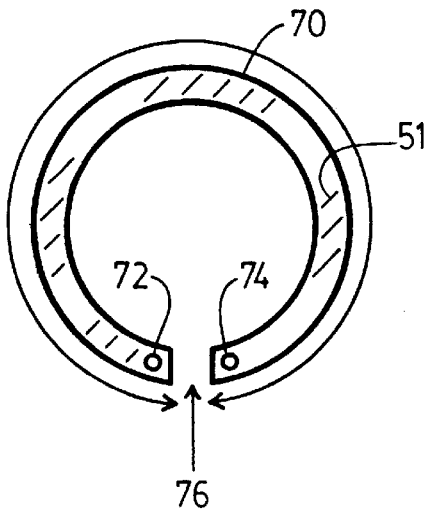
FIG._4A.
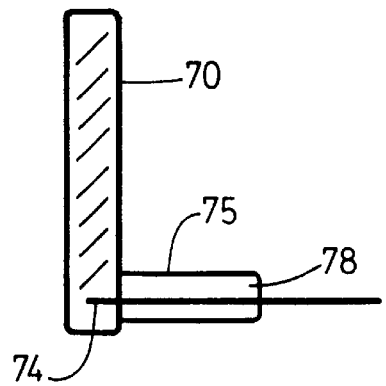
FIG._4B.
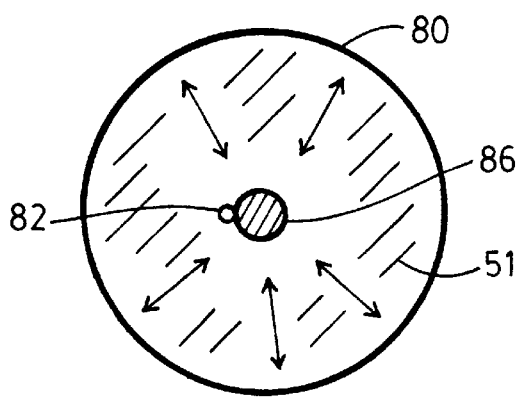
FIG._5A.
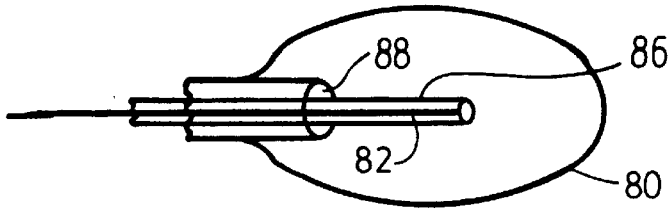
FIG._5B.

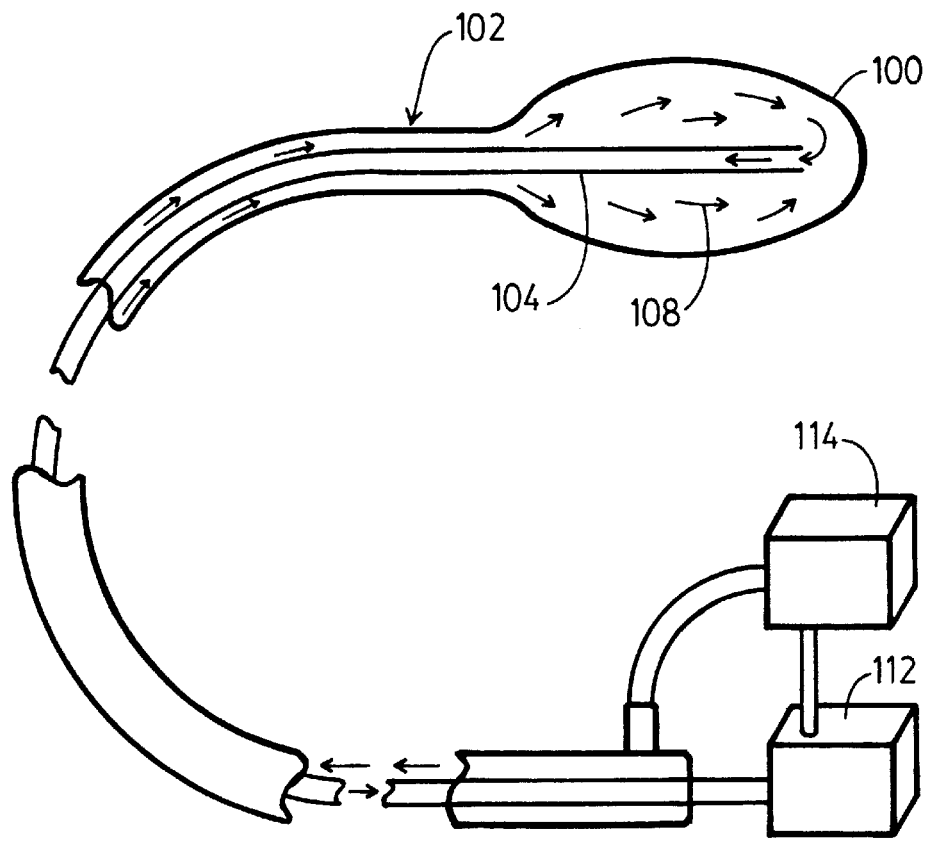
FIG._6.
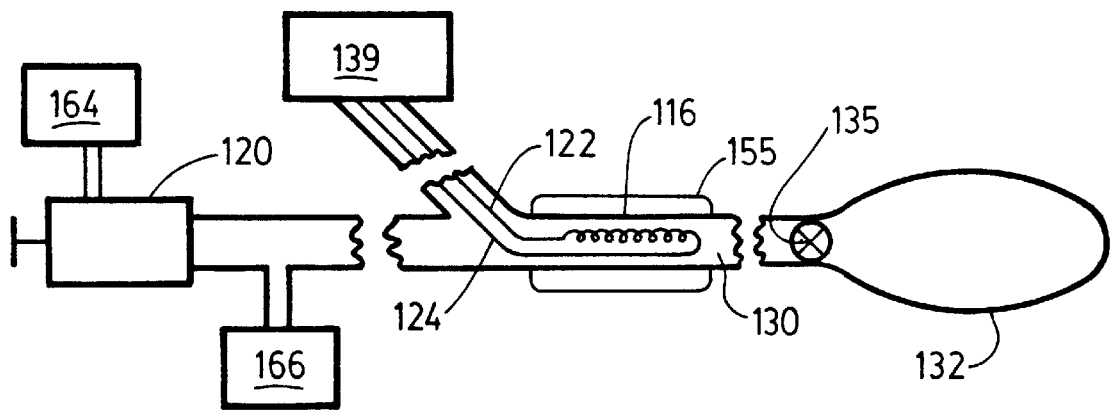
FIG._7.

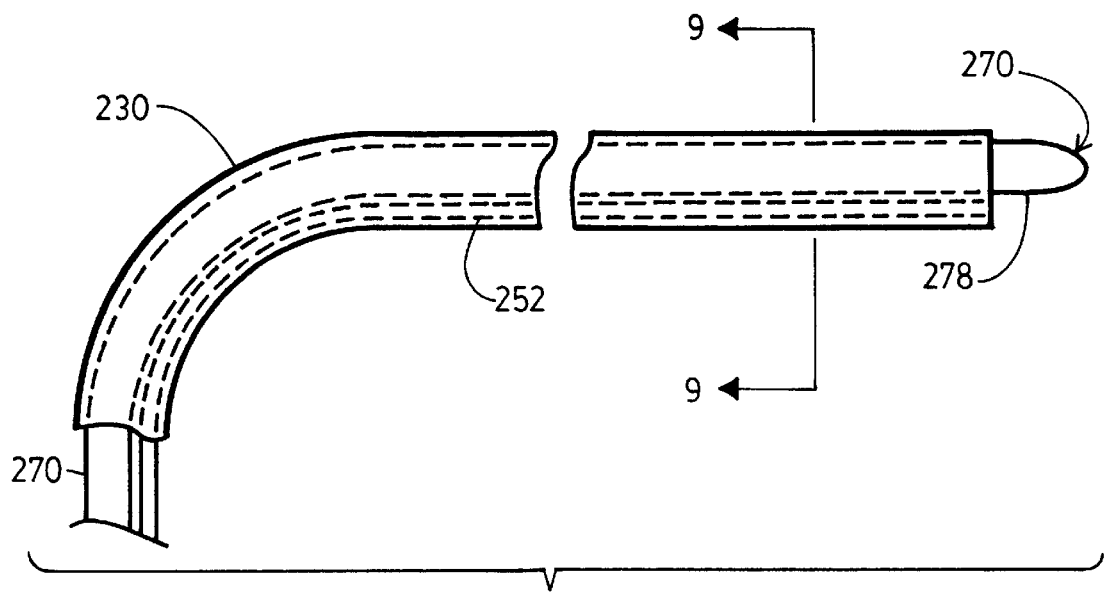
FIG._8.
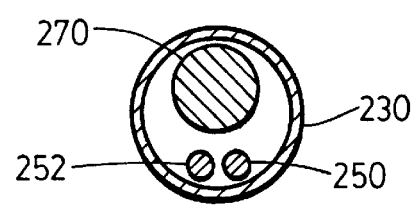
FIG._9.

BRONCHIAL STENTER

REFERENCE TO RELATED APPLICATION

This is a continuation-in-part application of application Ser. No. 08/833,550 filed on Apr. 7, 1997.

FIELD OF THE INVENTION

The present invention relates to a device and method for treatment of the airway obstruction found in chronic obstructive pulmonary diseases (COPD), such as cystic fibrosis, chronic bronchitis, emphysema, and asthma.

BACKGROUND OF THE INVENTION

Chronic obstructive pulmonary diseases (COPD), which includes such entities as cystic fibrosis, chronic bronchitis, and emphysema, are steadily increasing in frequency, possibly due to continued smoking, increasing air pollution, and the continued aging of the population. COPD is characterized by edema of the mucous membranes, which line the interior walls of the tracheobronchial tree. When the mucosa accumulates an abnormal quantity of liquid, the profuse and thickened serous fluid excreted may seriously affect ventilation in the alveoli. The mucus resists movement up the walls of the tracheobronchial tree, normally efficiently accomplished by the cilia throughout the airways which are also destroyed. Consequently, the serous fluid can form mucus plugs, which can shut off alveoli or entire airways. In addition to secretion accumulation, airway obstruction can occur because the tubes collapse due to destruction of connective tissue. This reduces the ability to get oxygen into the blood and carbon dioxide out of the blood.

Asthma is the most common form of bronchoconstrictive disease and pathologically involves constriction of the bronchioles, hypertrophy of the muscles of the bronchioles, and a characteristic infiltrate of eosinophils. Both asthma and COPD are characterized by the constriction or collapse of airway passages in the lungs that are not supported by cartilage. This condition is marked by labored breathing accompanied by wheezing, by a sense of constriction in the chest, and often by attacks of coughing and gasping. Individuals who are afflicted may attempt to compensate by blowing harder only to have the airways collapse further. A person with poor resulting ventilation suffers from a number of metabolic conditions including accumulation of carbon dioxide. These individuals also often have hyperinflated enlarged lungs and barrel-shaped chests.

A wide variety of drugs are available for treating the symptoms of COPD but none is curative. Cystic fibrosis, chronic bronchitis, and emphysema are typically treated with agents to thin and dry up the secretions and with antibiotics to combat infection and with bronchodilators. These drugs include potassium iodide, antihistamines, various antibiotics, beta agonists and aminophylline. Unfortunately, a large number of patients are not responsive to these medications or become non-responsive after prolonged periods of treatment. For severe cases involving collapsed air passages, surgeons have endeavored to alleviate this disabling condition by either (1) removing a portion of the lungs or (1) constricting the volume of lung available for respiration by stapling off sections thereof. The result is that functionally the diaphragm and muscles in the chest wall operate on a smaller lung volume which may improve air movement for some individuals. These operations are quite risky and are associated with a large number of deaths. Patients undergoing these treatments are quite ill and these procedures are considered final options.

Notwithstanding the conventional treatments available, there exists a need in the art for an effective treatment for chronic obstructive pulmonary diseases, such as cystic fibrosis, chronic bronchitis, emphysema and asthma. Specifically, there is a need for effective treatment for individuals with obstructed airway passages to restore pulmonary function which only requires minimal surgery.

SUMMARY OF THE INVENTION

The present invention is based in part on the discovery that the structural integrity of bronchial tubes, especially those which do not have significant amounts of cartilage present, can be significantly recreated by subjecting the bronchial tubes to a sufficient amount of heat to cause at least a portion of the cross links of the collagen fibers to open and subsequently form new cross links after the collagen fibers have realigned thereby causing the tubes to remain patent. This procedure changes the structure of the integral collagen and the shape of the tube.

In one aspect, the invention is directed to a method of selectively treating parts of a bronchial tube having a lumen which includes the step of heating the inner wall of the lumen to a temperature effective to cause collagen in the wall to undergo a structural transformation. Prior to treatment, the lumen can be non-collapsed, partially, or fully collapsed. Preferably, the bronchial tube is heated to a temperature in the range between about 60° C. and about 95° C. for about 1 to about 600 seconds.

In another aspect, the invention is directed to an apparatus, for treating a bronchial tube having a lumen, that includes:

a treatment device comprising an elongated member with a balloon that is attached to a distal end wherein the balloon deforms and expands upon the injection of a fluid into the interior of the balloon;

a source of fluid; and means for heating the fluid to a temperature sufficient to cause collagen in the wall of the lumen to undergo a structural transformation effective to render the wall capable of supporting a non-collapsed lumen.

In a further aspect, the invention is directed to an apparatus, for treating a bronchial tube having a lumen, that includes:

a treatment device comprising an elongated member with a balloon that is attached to a distal end wherein the balloon deforms and expands upon the introduction of a heated fluid into the balloon;

a source of the heated fluid; and means for introducing the heated fluid into the balloon.

In yet another aspect, the invention is direction to a modified lung wherein a bronchial tube having a collapsed or partially collapsed lumen that has been treated by a process that comprises the step of:

heating the wall of the lumen to a temperature effective to cause collagen in the wall to undergo a structural transformation to render the wall capable of supporting a non-collapsed lumen.

BRIEF DESCRIPTION OF THE DRAWINGS

As used herein, like reference numerals will designate similar elements in the various embodiments of the present invention wherein:

FIG. 1A is a schematic view of an embodiment of the device of the present invention.

FIG. 1B is an enlarged view of the circled portion of FIG. 1A.

FIG. 1C is an alternative embodiment to the device of FIG. 1A wherein each balloon includes a suitable set of bipolar electrodes and the balloons are connected to a separate or common fluid source.

FIGS. 2A, 2B, 3A, 3B, 4A, 4B, 5A, and 5B illustrate additional embodiments of the heat treatment device which employ RF energy.

FIG. 6 illustrates an embodiment of the heat treatment device which employs circulating heated fluid.

FIG. 7 illustrates an embodiment of the heat treatment device that has both resistive heating and inductive heating.

FIGS. 8 and 9 are cross-sectional views of a bronchoscope with a treatment device positioned therein.

DETAILED DESCRIPTION OF THE PREFERRED EMBODIMENTS

Many types of tissue can be molded and remodeled to correct defects and dysfunction. One technique involves physical manipulation using mechanical instruments and/or balloons to effect selective shrinking, stretching, flattening, thinning or thickening in addition to changing the material properties of the tissue. These changes of properties include alteration of the elastic coefficient of the tissue causing it to be stiffer, changing the tensile strength of the tissue, changing the shear strength of the tissue, and changing the floppiness or resiliency of the tissue. When the tissue is close to the surface of the skin or part of a non-critical organ, physical manipulation is feasible and can be executed with minimal trauma to the patient. However, when the tissue is in an internal organ, in particular, in the lungs or other vital organ, molding and remodeling by physical manipulation can involve complicated and often risky surgery.

Molding or remodeling or sterilizing of certain soft tissue, e.g., collagen, can also be carried out using heat. The heat can be applied conductively to the tissue through contact with a heated surface which has in turn been heated by, for example, a heated fluid.

With the inventive procedure, extensive surgery and the accompanying trauma is avoided. Specifically, the invention provides for a method for treating a bronchial tube which comprises the steps of:

1) maneuvering a heating device into the lumen of the bronchial tube;
2) causing the heating device to heat the tissue of the bronchial tube and continue the heating to cause collagen in the wall of the lumen to undergo a structural transformation effective to render the wall capable of supporting the lumen without collapsing; and
3) removing the device from the patient's bronchus airway.

This invention is particularly useful for treating subjects experiencing difficulty in breathing as a result of obstructed airway passages caused by, for example, chronic obstructive pulmonary disease, including, for example, cystic fibrosis, chronic bronchitis, emphysema, and asthma. This invention ameliorates the effects of these diseases by improving lung function by keeping the airway passages open. Specifically, the present invention provides a device and method for effecting changes in collagen-containing soft tissue in the bronchial tubes or air passages of the lungs which have collapsed. The causes of the collapse may be the destruction of the connective tissue, the disease process, swelling, and/or muscle-dependant constriction. The invention is directed to a treatment process which effectively creates an internal bronchial stent which prevents the air passages from collapsing. As used herein, the term "bronchial tube" or "air passage" refers to the sub-segments that branch from the main stem bronchus of the lungs. The term "collapsed lumen" refers to a condition of lumen of a bronchial tube wherein the lumen is occluded to the extent that substantial blockage of air flow through the lumen exists. The diameter of a non-collapsed lumen may be substantially equal to that of a normal bronchial tube or may be less as in the case of a partially collapsed but functional lumen. It is understood that the term "non-collapsed lumen" encompasses partially collapsed lumens. Cartilage is not present around these air passages in appreciable amounts so they have little intrinsic supportive structures.

In one embodiment the device comprises a catheter having a heat producing, i.e., direct heating or heat inducing, means at the end which is positioned in contact with, or in close proximity to the wall of a bronchial tube. The direct heating means include electrical resistance. Regardless of the source, energy delivered to the lumen wall of the airway passage should be such that none of the tissue is ablated.

FIG. 1A shows one embodiment of the device of the present invention which includes a balloon 12 placed at the distal end of a catheter shaft 16. The catheter shaft is connected to syringe 20 located at the proximal end and is connected to an RF generator 30 in between the syringe and balloon. As shown in FIG. 1B which is an enlarged, cut away view of the device, the balloon 12, which is illustrated in the non-inflated state, is constructed of an elastomeric material 22. A preferred elastomeric material is silicone. Extending from lumen 26 of the shaft and into the interior of the balloon are electrodes 32 and 34 which are spaced apart and supported by rod 36. In this embodiment, each electrode is configured as a loop or ring around the rod. Catheter shafts suitable for use in the present invention are substantially any of the catheter shafts in current clinical use for surgical procedures. Balloons suitable for the present invention may be of similar material and design as those currently being used in percutaneous transluminal angioplasty. For a review of the state of the art, see U.S. Pat. Nos. 4,807,620; 5,057,106; 5,190,517; 5,281,218; 5,314,466; 5,370,677; 5,370,678; 5,405,346; 5,431,649; 5,437,664; 5,447,529; and 5,454,809 all incorporated herein by reference. The inventive heat treatment devices will be described using balloons that are fabricated from an elastomeric material such as, for instance, silicone, natural latex, and polyethylene. The material selected must not melt at the temperature ranges used in the treatment and must be substantially impervious to the fluid used to inflate the balloon. With balloons that are made of elastomeric materials, the degree of expansion is proportional to the amount of force introduced into the interior of the balloon. Moreover, the balloon preferably will substantially return to its original, non-expanded form when the internal force is deactivated. When the balloon is fully expanded, its diameter will preferably be about 1 mm to 30 mm depending on the site to be treated. The balloon is typically attached to the catheter tip and the balloon material is folded or collapsed so that when it is fully inflated the balloon diameter has a fixed dimension. It is understood however that other balloon structures can be employed. For example, balloons made of non-elastic materials such as, for example, polyester (e.g., MYLAR) and polyethylene, can also be used. As is apparent, the balloon serves as a vessel or reservoir for medium that is heated. In the case where the electrodes are bipolar electrodes, the fluid (e.g., saline) between the poles acts as a resistive heating medium or resistive element. In addition, the balloon upon being inflated serves as structural support for the bronchial tubes.

Referring to FIGS. 1A and 1B, electrodes 32 and 34 are connected via cables 40 and 42, through the wall of the balloon 12, and through the catheter shaft 16 to a radio frequency (RF) generator 30 with controls 38. The catheter shaft 16 is also connected to a syringe 20 or other similar device for forcing a non-compressible fluid, such as saline, from source 46 through valve 48 to inflate the balloon with the fluid as the operating surgeon deems appropriate.

The frequency range of RF radiation useful in the present invention is typically about 10 KHZ to about 100 MHZ and preferably in the range of about 10 KHZ to about 800 KHZ. However, frequencies outside this range may be used at the discretion of the operating surgeon. Alternatively, microwave radiation typically in the frequency range of about 1,000 MHZ to about 2,000 MHZ, preferably in the range of about 1,100 MHZ to about 1,500 MHZ, may be used in place of RF radiation. However, as above, frequencies outside this range may be used at the discretion of the operating surgeon. The RF generator 30 is replaced with a microwave generator, and the cables 40 and 42 are replaced with a waveguide. Other modifications familiar to those skilled in the art may also be required. In addition, alternating current can be employed.

In use, when the operating surgeon has placed the treatment device with the collapsed balloon within the lumen of a bronchial tube to be treated, the balloon is inflated through the catheter shaft 16 with fluid from a syringe 20 located conveniently for the surgeon. In the case where the lumen of the bronchial tube has collapsed or is partially collapsed, the balloon is preferably inflated until the lumen has expanded to its normal diameter with the balloon in substantial contact with the inner surface of the lumen. Alternatively, in the case where the lumen has not collapsed, the balloon is preferably inflated until it is in substantial contact with the inner surface of the lumen. Indeed, inflation of the balloon is not necessary in treating a non-collapsed bronchial lumen which has a diameter that is about equal to, or less than that of the outer surface of the uninflated balloon. As is apparent, even if the balloon does not have to be inflated, the balloon interior has fluid, e.g., electrically conductive saline, present which becomes heated by the application of RF energy.

Preferably, the exact amount of inflation is determined by the operating surgeon who monitors the balloon expansion by means of endoscopy, or other suitable imaging methods of the art. Generally, the heat required is induced in the tissue of the bronchial tube wall by the RF or microwave radiation emitting from the balloon tip. The RF or microwave energy would be applied while observing for changes via simultaneous endoscopy, or other suitable imaging methods of the art.

As is apparent, the inventive heat treatment devices can be employed to treat a bronchial tube regardless of whether its lumen has collapsed or not. Specifically, the devices can be used to treat bronchial tubes that have not collapsed, are partially collapsed, or are fully collapsed. Moreover, bronchial tubes may exhibit different degrees of closure depending on the state of respiration. For example, a bronchial tube may have a fully expanded lumen after inhalation but partially or completely closed during exhalation.

FIGS. 2A, 2B, 3A, 3B, 4A and 4B illustrate other embodiments of the electrode configurations which can be employed with the treatment device shown in FIG. 1A. In these figures, the balloons are shown in the inflated state containing fluid 51. The arrows depict the path of the electric field between the two electrodes or probes that serve as RF poles.

In FIG. 2A, which is a cross-sectional view of balloon 50, electrodes 52 and 54 are configured as elongated wires that are attached at opposite sides of nonconductive rod 56. FIG. 2B is a side view of the balloon with the electrodes inside the interior of the balloon which is sealed except for conduit 58 through which fluid 51 (e.g., saline) is introduced and removed.

In FIG. 3A, which is a cross-sectional view of the balloon 60, electrodes 62 and 64 are wires each configured as a semi-circle and positioned at opposite sides of each other to form a circle. The electrodes have opposite polarities and are electrically insulated from each other. FIG. 3B is a side view of the balloon with the electrodes inside the interior of the balloon which is sealed except for conduit 68 through which fluid 51 is introduced and removed.

In FIG. 4A, which is cross-sectional view of the balloon 70, electrodes 72 and 74 are wires with tips that protrude into the interior region of the balloon which has a hollow disk or horse shoe configuration with partition 76 separating the two halves of the disk. Fluid 51 is introduced and removed from the balloon through conduit 78 in support member 75. The electrodes remain stationary in the solid regions of support member 75 as shown in side view FIG. 4B.

FIGS. 5A and 5B illustrate another embodiment in which the balloon 80 is fabricated of an electrically conductive material and therefore also serves as an electrode. In this fashion, one of the electrodes is an integral part of the balloon itself. The second electrode 82 is attached to nonconducting rod 86. FIG. 5B is a perspective view of the balloon with electrode 82 in the interior of the balloon which is sealed except for conduit 88 through which fluid 51 is introduced and removed. Suitable electrically conductive materials for fabricating the balloon in this case include, for example, a polyester film (e.g. MYLAR) that is coated with gold, silver, or platinum.

The above embodiments illustrate heating devices that comprise a bipolar electrode. In each device the electrodes emit RF energy with the first conductive element acting as the active electrode and the second conductive element acting as the return electrode, or vice versa. One electrode would be connected to the positive electrode of the generator and the other would be connected to the negative electrode. An insulator is located between the conductive elements.

FIG. 6 shows another embodiment of the device of the present invention wherein the heat generated to heat the fluid in the balloon is supplied by a circulating, hot fluid. Referring to FIG. 6, a balloon 100 (substantially the same as balloon 12 of the first embodiment as shown in FIG. 1A) is attached to a catheter 102 containing a smaller, coaxial catheter 104 (coaxial catheter 102 is substantially the same as catheter 104 differing only in size.) A heated fluid 108, which may be a liquid, such as water or physiologically compatibly saline solution, is pumped by a metering, circulating pump 112, through a heating unit 114, then through the outer catheter 102 to the balloon. The fluid heats the surface of the balloon and exits through the inner coaxial catheter 104 to return to the pump. A positive pressure is maintained within the system to keep the balloon at the proper inflation. This embodiment is employed in substantially the same manner as the other embodiments described above regarding its use to heat the wall of a bronchial tube. The choice of the temperature of the circulating liquid is at the discretion of the operating surgeon, but will usually be in the range of about 60° C. to about 95° C.

The heat treatment device shown in FIG. 7 represents another embodiment of the treatment device of the present invention wherein the heat generated to heat the fluid in the balloon is supplied by a hot fluid that is injected into the balloon. The catheter 116 includes electrodes 122 and 124 positioned in lumen 130 of the catheter. The electrodes are connected to AC generator 139 although an RF generator can also be used. The channel or lumen 130 also serves as a reservoir for liquid which is introduced from source 164 through syringe 120. Once the fluid is heated to the desired temperature, it can be injected into the interior of the balloon. As is apparent, the fluid serves both to inflate the balloon as well as to supply the heat treatment of the bronchial tube. A positive pressure is maintained within the system to keep the balloon at the proper inflation. Instead of using resistive heating, the fluid can be heated with heat exchanger 116.

The function of the treating element is to apply a sufficient amount of energy to the walls of air passages to cause collagen in the walls to undergo a structural transformation to create more rigid walls that can support a noncollapsed, patent lumen.

RF energy is no longer applied after there has been sufficient transformation, e.g., shrinkage, of the collagen fibers which may be gauged by removing the heating device from the treatment site and visually determining whether the lumen remains uncollapsed. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method.

Substantial transformation may be achieved very rapidly depending upon the specific treatment conditions. Because the transformation can proceed at a rather rapid rate, the RF energy should be applied at low power levels. Preferably, the RF energy is applied for a length of time in the range of about 1 second to about 600 seconds and preferably about 5 to about 120 seconds. Suitable RF power sources are commercially available and well known to those skilled in the art. In one embodiment the RF generator employed has a single channel that is capable of delivering approximately 1 to 100 watts and preferably 1 to 25 watts of RF energy and possesses continuous flow capability. The rate of collagen transformation can be controlled by varying the energy delivered to the balloon exterior surface. Regardless of the source of energy used during treatment, the lumen or the bronchial tube is maintained at a temperature of at least about 60° C. and typically between 70° C. to 95° C. and preferably between 70° C. to 85° C.

The treatment apparatus may comprise more than one balloon and attendant bipolar electrodes which are positioned along the length of the elongated member so that a plurality of locations along a bronchial tube can be treated simultaneously. FIG. 1C illustrates an alternative embodiment to the device of FIG. 1A described above are includes two balloons 12A and 12B that are spaced apart. Each balloon includes a suitable set of bipolar electrodes as described previously. The balloons can be connected to separate sources of fluid or they can share a common source.

In operation, when treating a person with obstructed air passages, a preliminary assessment is made to identify the air passages or bronchial tubes that can be treated. In treating a particular site, excessive fluid is first removed from the obstructed air passage by conventional means such as with a suction catheter. Thereafter, the catheter of the inventive heat treatment device is maneuvered to the treatment site. Depending on the diameter of the lumen of the bronchial tube, the catheter can be positioned directly at the treatment site or it can be positioned into place with a bronchoscope.

The shaft of the catheter is made of a flexible material so that it can be maneuvered through a bronchoscope. A bronchoscope is a modified catheter which is an illuminating instrument for inspecting and passing instruments (e.g., the treatment device) into the bronchial tubes.

FIGS. 8 and 9 illustrate a bronchoscope 230 having treatment apparatus 270 slidably positioned within a lumen. The device also includes an image-transmitting fiber 250 and illuminating fiber 252. Any conventional bronchoscope with an appropriately sized and directed working lumen may be employed. The image transmitting fiber collects light from the distal end of the treating apparatus and directs the light to a viewing apparatus (not shown) for displaying an image of the obstructed air passage. The bronchoscope may have a panning system which enables the tips to be moved in different directions.

The bronchoscope is advanced from the person's nasal or oral cavity, and through the trachea, main stem bronchus, and into an obstructed air passage. The heat treatment device is connected to an RF generator located remotely from the patient. The treatment device is advanced forward from the bronchoscope to expose the tip containing the balloon before the RF generator is energized. Depending on the size of the balloon, the treatment device can be moved to another position for further heat treatment of the air passage. This process can be repeated as many times as necessary to form a series of patency bands supporting an air passage. This procedure is applied to a sufficient number of air passages until the physician determines that he is finished. As is apparent, the procedure can be completed in one treatment or multiple treatments. After completion of each treatment, RF is the deactivated and the balloon is deflated. The bronchoscope is then removed from the patient.

The heating apparatus can be made to provide protection against overheating of the connective tissue which will cause the collagen to denature. Temperature monitoring and impedance monitoring can be utilized in a system which provides feedback to the user in the form of sounds, lights, other displays or which shuts down the application of energy from the heating element to the treatment site when sufficient transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as to modulate the power. The microprocessor can serve as a controller to monitor the temperature and modulate the power.

The invention is also directed to the demonstration or instruction of the inventive surgical techniques including, but not limited to, written and actual instructions involving patients, audio-visual presentations, animal demonstrations, and the like.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. A method of treating a bronchial tube comprising a lumen in an individual that comprises the step of:

heating a wall of the lumen with an expandable heat treatment device to a temperature effective to cause the wall to undergo a structural transformation to improve the structural integrity of the wall.

2. The method of claim 1 wherein the wall is heated to a temperature in the range between about 60° C. and about 95° C.

3. The method of claim 2 wherein the wall is heated for about 1 to about 600 seconds.

4. The method of claim 1 wherein the step of heating the wall comprises:
   advancing a treatment device into the lumen of the bronchial tube; and
   activating the treatment device to raise the temperature of the wall to cause a structural transformation in the collagen of the wall.

5. A method of treating a bronchial tube comprising a lumen in an individual that comprise the step of:
   heating a wall of the lumen to a temperature effective to cause the wall to undergo a structural transformation to improve the structural integrity of the wall, wherein the treatment device comprises:
      an elongated member with a balloon that is attached to a distal end wherein the balloon deforms and expands upon the injection of a fluid into the interior of the balloon;
      a source of fluid; and
      means for heating the fluid to a temperature sufficient to cause the wall of the lumen to undergo a structural transformation effective to render the wall capable of supporting a non-collapsed lumen.

6. The method of claim 5 wherein the means for heating the fluid comprises:
   a source of energy; and
   means for transmitting energy from the source of energy to the fluid.

7. The method of claim 5 wherein the means for heating the fluid comprises at least two electrodes.

8. The method of claim 5 wherein the means for heating the fluid comprises a first electrode which is connected to the positive electrode of an RF generator and a second electrode which is connected to the negative electrode of the RF generator.

9. The method of claim 8 wherein the first electrode has a first pole and the second electrode has a second pole that are located in the interior of the balloon and are in contact with the fluid.

10. The method of claim 6 wherein the source of energy generates RF energy or alternating current.

11. The method of claim 5 wherein the fluid is saline.

12. The method of claim 5 wherein the balloon is made of an elastic material.

13. The method of claim 5 wherein the balloon is made of an inelastic material.

14. The method of claim 5 wherein the fluid is saline.

15. A method of treating a bronchial tube comprising a lumen in an individual that comprises the step of:
   heating a wall of the lumen to a temperature effective to cause the wall to undergo a structural transformation to improve the structural integrity of the wall, wherein the treatment device comprises:
      an elongated member with a balloon that is attached to a distal end wherein the balloon deforms and expands upon the introduction of a heated fluid into the balloon;
      a source of fluid; and
      means for introducing the heated fluid into the balloon.

16. The method of claim 15 wherein the source of heated fluid comprises:
   at least one electrode locating in the elongated member and which when energized heats a fluid to a temperature sufficient to cause the wall of the lumen to undergo a structural transformation effective to render the wall capable of supporting a non-collapsed lumen;
   a source of energy; and
   means for transmitting energy from the source of energy to the at least one electrode.

17. The method of claim 16 wherein the at least one electrode comprises a first electrode which is connected to the positive electrode of an RF generator and a second electrode which is connected to the negative electrode of the RF generator.

18. The method of claim 16 wherein the source of energy generates RF energy or alternating current.

19. The method of claim 15 wherein the fluid is saline.

20. The method of claim 15 wherein the means for introducing the heated fluid includes means for circulating a heated fluid into and out of the balloon.

21. The method of claim 15 wherein the balloon is made of an elastic material.

22. The method of claim 15 wherein the balloon is made of a non-elastic material.

23. A method of training a person to treat a bronchial tube comprising a lumen of an individual that comprises demonstrating or instructing the performance of the following steps:
   heating a wall of the lumen with an expandable heat treatment device to a temperature effective to cause the wall to undergo a structural transformation to improve the structural integrity of the wall.

24. The method of claim 23 wherein the wall is heated to a temperature in the range between about 60° C. and about 95° C.

25. The method of claim 24 wherein the wall is heated for about 1 to about 600 seconds.

26. The method of claim 23 wherein the step of heating the wall comprises:
   advancing a treatment device into the lumen of the bronchial tube of the individual; and
   activating the treatment device to raise the temperature of the wall to sufficiently effect a structural transformation of the wall.

27. The method of claim 26 wherein the treatment device comprises:
   a treatment device comprising an elongated member with a balloon that is attached to a distal end wherein the balloon deforms and expands upon the injection of a fluid into the interior of the balloon;
   a source of fluid; and
   means for heating the fluid to a temperature sufficient to cause the wall of the lumen to undergo a structural transformation effective to render the wall capable of supporting a non-collapsed lumen.

28. The method of claim 26 wherein the treatment device comprises:
   an elongated member with a balloon that is attached to a distal end wherein the balloon deforms and expands upon the introduction of a heated fluid into the balloon;
   a source of the heated fluid; and
   means for introducing the heated fluid into the balloon.

29. A method of treating a bronchial tube comprising:
   heating a wall of the bronchial tube to a temperature of at least 70° C. to cause the wall to undergo a structural transformation to improve the structural integrity of the wall.

30. The method of claim 29 wherein the wall is treated with a treatment device having an expandable distal end for contacting and heating the bronchial tube wall.

31. The method of claim 29 wherein the wall is heated to a temperature of about 70° C. to about 95° C.

32. The method of claim 29 wherein the step of heating the wall comprises:

advancing a treatment device into the lumen of the bronchial tube; and activating the treatment device to raise the temperature of the wall to at least 70° C. to cause the structural transformation and improve the integrity of the wall.

* * * * *